(12) United States Patent
Funke et al.

(10) Patent No.: US 7,060,857 B2
(45) Date of Patent: Jun. 13, 2006

(54) METHOD FOR THE PRODUCTION OF ISOPHORONDIAMINE (IPDA,3-AMINO-METHYL-3,5,5-TRIMETHYLCYCLO-HEXYLAMINE)

(75) Inventors: Frank Funke, Mannheim (DE); Thomas Hill, Mannheim (DE); Johann-Peter Melder, Böhl-Iggelheim (DE); Ekkehard Schwab, Neustadt (DE); Walter Himmel, Grünstadt (DE); Erhard Henkes, Einhausen (DE); Hermann Petersen, Grünstadt (DE); Reinhard Körner, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 102 days.

(21) Appl. No.: 10/487,609

(22) PCT Filed: Aug. 28, 2002

(86) PCT No.: PCT/EP02/09600

§ 371 (c)(1),
(2), (4) Date: Feb. 24, 2004

(87) PCT Pub. No.: WO03/020421

PCT Pub. Date: Mar. 13, 2003

(65) Prior Publication Data

US 2004/0225156 A1    Nov. 11, 2004

(30) Foreign Application Priority Data

Aug. 31, 2001 (DE) ................................ 101 42 635

(51) Int. Cl.
*C07C 211/36* (2006.01)
*B01J 27/185* (2006.01)

(52) U.S. Cl. .................... 564/455; 564/448; 502/213

(58) Field of Classification Search .................... None
See application file for complete search history.

(56) References Cited

U.S. PATENT DOCUMENTS

| | | | |
|---|---|---|---|
| 5,373,068 A | 12/1994 | Piana et al. | |
| 5,504,254 A | 4/1996 | Haas et al. | |
| 5,536,691 A | * 7/1996 | Breitscheidel et al. | ...... 502/213 |
| 5,583,260 A | 12/1996 | Haas et al. | |
| 5,696,048 A | 12/1997 | Breitscheidel et al. | |
| 5,756,845 A | 5/1998 | Voit et al. | |
| 6,022,999 A | 2/2000 | Voit et al. | |

FOREIGN PATENT DOCUMENTS

| | | |
|---|---|---|
| DE | 4 211 454 | 10/1993 |
| DE | 4 343 890 | 6/1995 |
| DE | 4 343 891 | 6/1995 |
| EP | 0 729 937 | 9/1996 |
| EP | 0 742 045 | 11/1996 |
| EP | 0 926 130 | 6/1999 |

OTHER PUBLICATIONS

DW 93-321 708 (DE 4211454-X1 abstract 1993).
DW 95-226 187 (DE 4343891 abstract 1995).

* cited by examiner

*Primary Examiner*—Brian Davis
(74) *Attorney, Agent, or Firm*—Novak Druce & Quigg, LLP; Jason D. Voight

(57) ABSTRACT

In a process for preparing 3-aminomethyl-3,5,5-trimethyl-cyclohexylamine (isophoronediamine, IPDA) having a cis/trans isomer ratio of at least 70/30 from 3-cyano-3,5,5-trimethylcyclohexanone (isophoronenitrile, IPN), $NH_3$ and $H_2$, the hydrogenation is carried out at from 50 to 200° C. and a pressure of from 50 to 300 bar in the presence of a hydrogenation catalyst having an alkali metal content of $\leq 0.03\%$ by weight, calculated as alkali metal oxide referring to the total weight of the catalyst.

The alkali metal content is made up of the contents of Li, Na, K, Rb and Cs; in particular, the alkali metal content is the Na content.

A process for producing hydrogenation catalysts having an alkali metal content (in particular a sodium content) of $\leq 0.03\%$ by weight, calculated as alkali metal oxide/sodium oxide referring to the total weight of the catalyst, and the hydrogenation catalysts themselves are also provided by the invention.

12 Claims, No Drawings

METHOD FOR THE PRODUCTION OF ISOPHORONDIAMINE (IPDA,3-AMINO-METHYL-3,5,5-TRIMETHYLCYCLO-HEXYLAMINE)

The present invention relates to a process for preparing 3-aminomethyl-3,5,5-trimethylcyclohexylamine (isophoronediamine, IPDA) having a cis/trans isomer ratio of at least 70/30 from 3-cyano-3,5,5-trimethylcyclohexanone (isophoronenitrile, IPN), $H_2$ and $NH_3$, where the hydrogenation is carried out in the presence of a hydrogenation catalyst whose alkali metal content is $\leq 0.03\%$ by weight, calculated as alkali metal oxide. The invention further relates to a process for producing such catalysts and to the catalysts themselves.

IPDA is used as starting material for preparing isophorone diisocyanate (IPDI), an isocyanate component for polyurethane systems, as amine component for polyamides and as hardener for epoxy resins. IPDA is usually prepared from IPN, with the carbonyl group being converted into an amino group and the nitrile group being converted into an aminomethyl group in the presence of ammonia, hydrogen and customary hydrogenation catalysts. This gives mixtures of cis-IPDA and trans-IPDA. The two isomers have different reactivities, which is of importance in the intended industrial application. According to DE-A 42 11 454 the use of an IPDA isomer mixture consisting of over 40% of the trans isomer and less than 60% of the cis isomer as reaction component in polyaddition resins, in particular epoxy resins, increases the pot life and decreases the maximum curing temperature. On the other hand, to achieve a very high reaction rate, preference is given to IPDA isomer mixtures which have a very high proportion of the cis isomer ($\geq 70\%$). For this reason, commercially available IPDA has a cis/trans isomer ratio of 75/25.

Various methods of achieving a high cis/trans ratio are already known:

According to DE-A 43 43 890, the aminative hydrogenation of IPN to IPDA is carried out by allowing a mixture of IPN, ammonia and a $C_1$–$C_3$-alcohol to trickle over a Co and/or Ru fixed-bed catalyst in a trickle-bed reactor at from 3 to 8 MPa and from 40 to 150° C., preferably from 90 to 130° C., in the presence of hydrogen and working up the reaction mixture by distillation. When using a supported Ru catalyst, high cis/trans ratios of 84/16 (total yield of IPDA: 81%) are achieved, while cis/trans ratios of only 60/40 are achieved when using a supported Co catalyst (total yield of IPDA: 87%). The combination of an Ru catalyst and a Co catalyst makes it possible to obtain IPDA in a cis/trans ratio which is similar to that obtained when only an Ru catalyst is used, but in a higher yield than when only this Ru catalyst is used.

DE-A 43 43 891 describes a process for preparing IPDA in which IPN is reacted with hydrogen at up to 150° C. and a pressure of from 3 to 20 MPa in the presence of ammonia and a suspended or fixed-bed hydrogenation catalyst selected from among Co, Ni and noble metal catalysts and the reaction mixture obtained is worked up by distillation. The particular feature of this process is that the reaction is carried out in two stages in precisely defined temperature ranges. A cis/trans isomer ratio of 80/20 can be achieved at a total IPDA yield of 91.9%.

In the process of EP-A 0 926 130, the hydrogenation is carried out in the presence of an acid over catalysts comprising copper and/or a metal of transition group VIII of the Periodic Table. Both Lewis and Brönsted acids are used; preference is given to using 2-ethylhexanoic acid. The cis/trans ratios are generally $\geq 70/30$ at a total IPDA yield of $\geq 90\%$.

The process of EP-B 0 729 937 is carried out in two physically separate reaction spaces using catalysts comprising cobalt, nickel, ruthenium and/or other noble metals. Aqueous NaOH solution is introduced upstream of the second reactor, which reduces the formation of cyclic by-products such as 1,3,3-trimethyl-6-azabicyclo[3.2.1]octane.

EP-A 0 742 045 describes cobalt catalysts whose catalytically active composition comprises from 55 to 98% by weight of cobalt, from 0.2 to 15% by weight of phosphorus, from 0.2 to 15% by weight of manganese and from 0.05 to 5% by weight, preferably from 0.1 to 3% by weight, particularly preferably from 0.13 to 1% by weight, of alkali metal, in each case calculated as oxide. These catalysts can be used in processes for the hydrogenation of organic nitrites and/or imines such as IPN at from 60 to 150° C. and pressures of from 50 to 300 bar. Nothing is said about the cis/trans ratio of the IPDA prepared in this way.

A disadvantage of the known processes for preparing IPDA is the formation of by-products which are difficult to separate off, e.g. HCN elimination products, methylated by-products and/or incompletely hydrogenated intermediates (see below).

It is an object of the present invention to provide a process for preparing isophoronediamine (IPDA) by means of which the disadvantages of the prior art can be avoided. In addition, a suitable catalyst and a process for producing this catalyst are to be found.

We have found that this object is achieved by a process for preparing 3-aminomethyl-3,5,5-trimethylcyclohexylamine (IPDA) having a cis/trans isomer ratio of at least 70/30 from 3-cyano-3,5,5-trimethylcyclohexanone (IPN), $NH_3$ and $H_2$, wherein the hydrogenation is carried out at from 50 to 200° C. and a pressure of from 50 to 300 bar in the presence of a hydrogenation catalyst having an alkali metal content of $\leq 0.03\%$ by weight, calculated as alkali metal oxide and referring to the total weight of the catalyst. The hydrogenation is preferably carried out at from 60 to 160° C., particularly preferably from 80 to 130° C., and pressures of from 100 to 250 bar, particularly preferably from 200 to 250 bar.

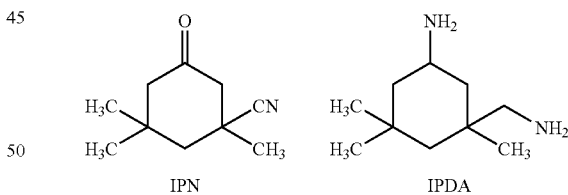

The alkali metal content is made up of the contents of Li, Na, K, Rb and Cs; in particular, the alkali metal content is the Na content.

If the processes for preparing IPDA using catalysts comprising alkali metals are compared with the process of the present invention using catalysts which are largely free of alkali metals, it is found that the reaction proceeds more selectively to the desired product IPDA when the catalysts of the present invention which are largely free of alkali metals are employed. The total formation of by-products is $\leq 10\%$ by area, preferably $\leq 7\%$ by area, particularly preferably $\leq 5\%$ by area, as determined by gas chromatography of the reaction product. Elimination of HCN occurs to a lesser extent (by-products IIa and IIb); in addition, virtually no methylated by-products (IIIa, IIIb) are formed. This is particularly advantageous, since these can be separated from the desired product IPDA only with difficulty. The amount of incompletely hydrogenated amino nitrile by-product (IV), which is very difficult to separate from IPDA by distillation, also decreases. Although more cyclic by-product 1,3,3-trimethyl-6-azabicyclo[3.2.1]octane (V) is formed, this is easy to separate of from IPDA by distillation.

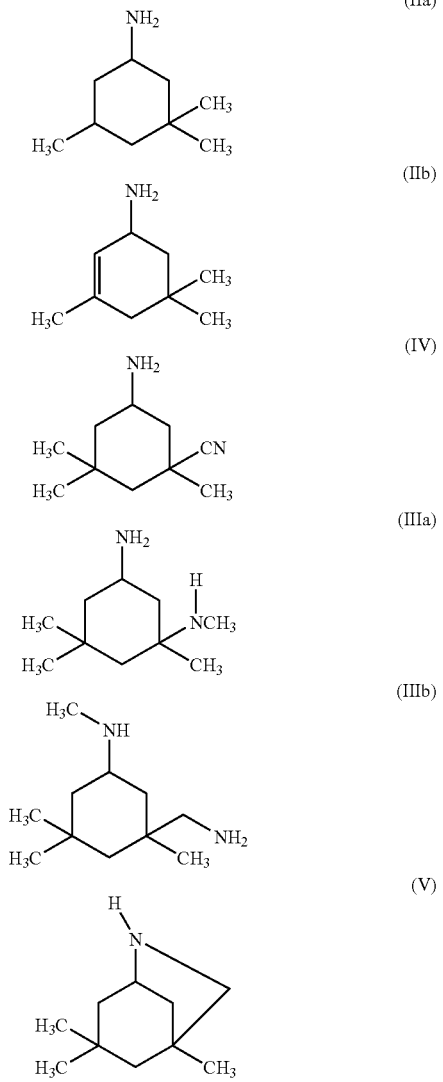

The process of the present invention enables cis/trans ratios of at least 70/30, preferably at least 73/27, particularly preferably at least 75/25, to be achieved. The cis/trans ratio can be determined, for example, by gas-chromatographic (GC) analysis of the reaction product. For this purpose, the measured area of the peak of cis-IPDA is divided by that of the peak of trans-IPDA.

The total yield of IPDA is generally ≧90%, in particular ≧93%, especially ≧95%. The purity is generally at least 98%, in particular at least 99%, especially from 99.3 to 99.7%, and can be determined by GC analysis of the reaction product.

In the conversion of IPN into IPDA, 3-cyano-3,5,5-trimethyl-cyclohexanonimine (I) is formed as intermediate.

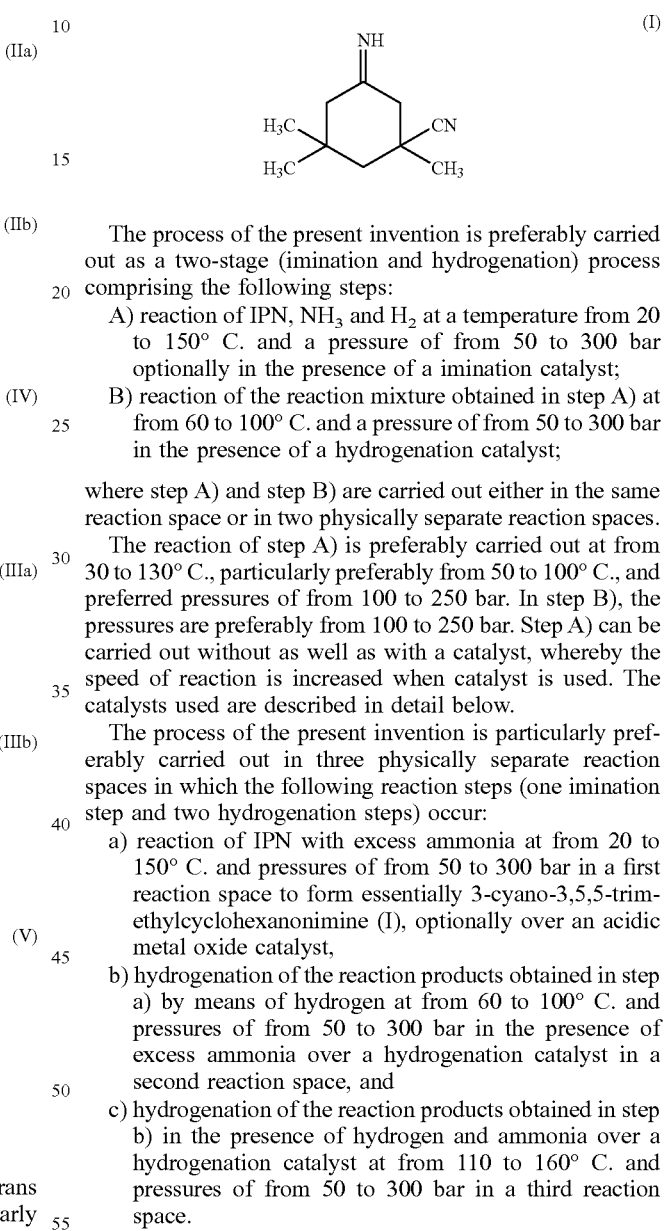

This imination is carried out, in particular, as separate step before the hydrogenation at temperatures from 20 to 150° C., preferably from 30 to 130° C., particularly preferably from 50 to 100° C., and pressures of from 50 to 300 bar, preferably from 100 to 250 bar, particularly preferably from 200 to 250 bar. The subsequent hydrogenation can then be carried out in one or two stages (see below).

The process of the present invention is preferably carried out as a two-stage (imination and hydrogenation) process comprising the following steps:

A) reaction of IPN, NH$_3$ and H$_2$ at a temperature from 20 to 150° C. and a pressure of from 50 to 300 bar optionally in the presence of a imination catalyst;

B) reaction of the reaction mixture obtained in step A) at from 60 to 100° C. and a pressure of from 50 to 300 bar in the presence of a hydrogenation catalyst;

where step A) and step B) are carried out either in the same reaction space or in two physically separate reaction spaces.

The reaction of step A) is preferably carried out at from 30 to 130° C., particularly preferably from 50 to 100° C., and preferred pressures of from 100 to 250 bar. In step B), the pressures are preferably from 100 to 250 bar. Step A) can be carried out without as well as with a catalyst, whereby the speed of reaction is increased when catalyst is used. The catalysts used are described in detail below.

The process of the present invention is particularly preferably carried out in three physically separate reaction spaces in which the following reaction steps (one imination step and two hydrogenation steps) occur:

a) reaction of IPN with excess ammonia at from 20 to 150° C. and pressures of from 50 to 300 bar in a first reaction space to form essentially 3-cyano-3,5,5-trimethylcyclohexanonimine (I), optionally over an acidic metal oxide catalyst, b) hydrogenation of the reaction products obtained in step a) by means of hydrogen at from 60 to 100° C. and pressures of from 50 to 300 bar in the presence of excess ammonia over a hydrogenation catalyst in a second reaction space, and c) hydrogenation of the reaction products obtained in step b) in the presence of hydrogen and ammonia over a hydrogenation catalyst at from 110 to 160° C. and pressures of from 50 to 300 bar in a third reaction space.

This three-stage process is described in detail below:

Step a)

In a first process step, IPN is reacted with excess ammonia at from 20 to 150° C., preferably from 30 to 130° C., particularly preferably from 50 to 100° C., and pressures of from 50 to 300 bar, preferably from 100 to 250 bar, in a first reaction space to form essentially 3-cyano-3,5,5-trimethyl-cyclohexanonimine (I).

Step a) can be carried out without as well as with a catalyst, whereby the speed of reaction is increased when a catalyst is used. Suitable acidic metal oxide catalysts are aluminum oxide, silicon dioxide, titanium dioxide, zirconium dioxide, activated carbon and mixtures thereof. Preference is given to using aluminum oxide, titanium dioxide, zirconium dioxide and mixtures thereof, in particular aluminum oxide and/or titanium dioxide.

In the imination, the space velocity over the catalyst is from 0.01 to 10, preferably from 0.05 to 7, particularly preferably from 0.1 to 5, kg of IPN per kg of catalyst and hour. Per mol of IPN, it is advantageous to use from 5 to 50 mol, preferably from 10 to 40 mol, particularly preferably from 20 to 30 mol, of $NH_3$ in the imination. The imination of the IPN can be carried out in the presence of a solvent, e.g. alkanols or tetrahydrofuran, but it is also possible to carry it out without addition of a solvent.

The imination is preferably carried out continuously, e.g. in pressure vessels or cascades of pressure vessels. In a particularly preferred embodiment, IPN and $NH_3$ are passed in the upflow mode or the downflow mode through a reactor in which the imination catalyst is located in the form of a fixed bed, or they are reacted with one another in a shaft oven.

Step b)

The reaction products obtained in step a) are subjected, in a second reaction space, to a catalytic hydrogenation using from 3 to 10000 molar equivalents, preferably from 4.5 to 100 molar equivalents, of hydrogen, if appropriate after introduction of further ammonia.

The hydrogenation is carried out at from 60 to 100° C. and a pressure of from 50 to 300 bar, preferably from 100 to 250 bar.

The space velocities over the catalyst are advantageously in the range from 0.01 to 5 kg of compound (I) per 1 of catalyst and hour [kg/l·h], preferably from 0.02 to 2.5 kg of compound (I) per 1 of catalyst and hour, particularly preferably from 0.05 to 2 kg of compound (I) per 1 of catalyst and hour.

The hydrogenation is preferably carried out in liquid ammonia. From 5 to 500 mol, preferably from 10 to 400 mol, particularly preferably from 20 to 300 mol, of $NH_3$ are used per mol of 3-cyano-3,5,5-trimethylcyclohexanonimine (I). It is advantageous to choose at least that amount of available $NH_3$ which is present after the preceding preparation of the compound I from IPN. However the proportion of $NH_3$ can also be increased to the desired value by addition of additional $NH_3$ before the hydrogenation.

The aminative hydrogenation of the reaction products obtained in step a) is preferably carried out continuously, e.g. in pressure-rated stirred vessels or in a cascade of stirred vessels. In a particularly preferred embodiment, reactors in which the product mixture from the imination is passed in the upflow mode or downflow mode over a fixed catalyst bed are used.

The output from the reactor may further comprise incompletely reacted components, e.g. the amino nitrile (IV) which is very difficult to separate from IPDA by distillation.

Step c)

The output obtained from the reactor in b) is, in a third step, reacted in the presence of hydrogen and ammonia at from 110 to 160° C. and from 50 to 300 bar, preferably from 100 to 250 bar. In step c) the same as well as another catalyst as used in step b) can be taken. It is advantageous to choose amounts of available ammonia and hydrogen which are present on leaving the reactor of step b).

In a preferred embodiment of the process of the present invention, the reactor used in step c) is significantly smaller than the reactor used in step b). For example, the reactor used in step c) has an empty volume corresponding to from 20 to 40% of the empty volume of the reactor used in step b).

After the hydrogenation, excess ammonia and any hydrogen are separated off, if desired under superatmospheric pressure. The crude IPDA obtained in this way is purified by fractional distillation.

In the process of the present invention for preparing IPDA from IPN, the hydrogenation catalysts used can in principle be any customary hydrogenation catalysts which have an alkali metal content of $\leq 0.03\%$ by weight, calculated as alkali metal oxide referring to the total weight of the catalyst, and comprise at least one transition metal selected from the group consisting of cobalt, ruthenium, nickel, iron, rhodium, palladium, osmium, iridium, platinum or copper. Preference is given to using ruthenium and cobalt catalysts and mixtures thereof which have an alkali metal content of $\leq 0.03\%$ by weight, calculated as alkali metal oxide referring to the total weight of the catalyst. Particular preference is given to cobalt catalysts having an alkali metal content of $\leq 0.03\%$ by weight, calculated as alkali metal oxide referring to the total weight of the catalyst. Furthermore, these cobalt catalysts may also be doped with from 0.01 to 10% by weight, preferably from 0.05 to 5% by weight, particularly preferably from 0.5 to 3% by weight, referring to the total weight of the catalyst of transition metals such as Ru, Ir, Pd, Pt and/or Ni.

In the process of the present invention, very particular preference is given to cobalt catalysts comprising from 55 to 98% by weight, preferably from 75 to 95% by weight, particularly preferably from 85 to 95% by weight, of cobalt, from 0.2 to 15% by weight, preferably from 0.5 to 10% by weight, particularly preferably from 1 to 6% by weight, of phosphorus, from 0.2 to 15% by weight, preferably from 2 to 10% by weight, particularly preferably from 3 to 8% by weight, of manganese and $\leq 0.03\%$ by weight of alkali metal, in each case calculated as oxide referring to the total weight of the catalyst. These cobalt catalysts may further comprise one or more promoters selected from the group consisting of ruthenium, palladium and nickel, preferably ruthenium and/or nickel, particularly preferably ruthenium, in an amount of from 0.01 to 10% by weight, preferably from 0.05 to 5% by weight, particularly preferably from 0.5 to 3% by weight, in each case calculated as oxide referring to the total weight of the catalyst.

The alkali metal content of these catalysts is preferably $\leq 0.015\%$ by weight, particularly preferably $\leq 0.01\%$ by weight, calculated as alkali metal oxide referring to the total weight of the catalyst. In particular, the sodium content of the catalysts described is $\leq 0.03\%$ by weight, preferably $\leq 0.015\%$ by weight, particularly preferably $\leq 0.01\%$ by weight, calculated as sodium oxide referring to the total weight of the catalyst. These catalysts having an alkali metal content of $\leq 0.03\%$ by weight, in particular a sodium content of $\leq 0.03\%$ by weight, calculated as alkali metal oxide referring to the total weight of the catalyst, are according to the present invention. The alkali metal or alkali metal oxide content can be determined by atomic absorption spectroscopy. The detection limit for alkali metals, in particular Na, in this method is 0.003% by weight.

In the three-stage process with the steps a), b) and c) only one of the two hydrogenation catalysts used in steps b) and c) is required to have an alkali metal content $\leq 0.03\%$ by weight, calculated as alkali metal oxide referring to the total weight of the catalyst. For the other catalyst this feature is optional.

The present invention likewise provides a process for producing a hydrogenation catalyst which has an alkali metal content of $\leq 0.03\%$ by weight, calculated as alkali metal oxide referring to the total weight of the catalyst, and comprises at least one transition metal selected from the group consisting of Co, Ru, Ni, Fe, Rh, Pd, Os, Ir, Pt and Cu, which comprises the following steps:

i) precipitating at least one of the abovementioned transition metals in the form of its carbonate, hydroxide and/or oxide from an aqueous solution comprising at least one water-soluble salt of one of the abovementioned transition metals by means of an aqueous solution comprising at least one substance selected from the group consisting of ammonium carbonate, ammonium hydrogen carbonate, ammonium carbamate, ammonium oxalate, ammonium malonate, ammonia and urotropin while stirring, with or without addition of promoters in the form of their water-soluble compounds;

ii) separating off the precipitate obtained in step i);

iiia) drying the resulting precipitate at from 50 to 200° C. and milling it to a catalyst powder, or iiib) slurrying the resulting precipitate and spray drying the resulting suspension at from 100 to 600° C., with or without addition of promoters in the form of their salts, to give a spray-dried catalyst powder;

iv) calcining the catalyst powder produced in step iiia) or iiib) at from 300 to 1000° C. and shaping it to form shaped catalyst bodies, with promoters being able, if desired, to be added in the form of their salts before and/or during and/or after shaping to form shaped catalyst bodies;

v) drying and calcining the shaped catalyst bodies produced in step iv);

vi) reducing the dried and calcined shaped catalyst bodies in an $H_2/N_2$ atmosphere at elevated temperature, with the composition of the $H_2/N_2$ atmosphere and the temperature being varied;

vii) optionally passivating the reduced shaped catalyst bodies at from 20 to 60° C., with promoters subsequently being applied in the form of their salts to the shaped catalyst bodies if desired.

The above-described process gives, in particular, hydrogenation catalysts having a sodium content of $\leq 0.03\%$ by weight. The process will now be described in detail, thus defining, for example, the term "elevated temperature" (step vi)). In the context of this process, room temperature encompasses temperatures of from 15 to 35° C., in particular from 20 to 30° C.

Step i)

An aqueous solution (precipitation solution) comprising at least one substance (precipitation reagent) selected from the group consisting of ammonium carbonate, ammonium hydrogen carbonate, ammonium carbamate, ammonium oxalate, ammonium malonate, ammonia and urotropin is added at from 30 to 90° C., preferably from 40 to 80° C., particularly preferably from 45 to 55° C., while stirring to an aqueous solution comprising at least one water-soluble salt of a transition metal selected from the group consisting of Co, Ru, Ni, Fe, Rh, Pd, Os, Ir, Pt and Cu, preferably at least one water-soluble inorganic salt of one of these transition metals, to precipitate at least one of the abovementioned transition metals in the form of its carbonate, hydroxide and/or oxide. If ammonium carbonate or ammonium hydrogen carbonate is used as precipitation reagent, the pH employed is generally from 5.5 to 9.0, preferably from 6.0 to 8.0, particularly preferably from 6.2 to 6.8. If ammonium carbamate, ammonium oxalate, ammonium malonate, ammonia and/or urotropin are employed for the precipitation, the pH of the precipitated solution is generally $\leq 5$, preferably $\leq 2$, particularly preferably $\leq 1.5$. Among the transition metal salts indicated, preference is given to using Co and Ru salts, particularly preferably Co salts. Among the precipitated reagents, preference is given to using ammonium carbonate. The transition metal salt solution may further comprise desired promoters such as manganese, phosphorus and/or ruthenium in the form of their water-soluble compounds.

The concentrations both of the transition metal salt solution and of the precipitation solution should be set so that the resulting precipitation slurry can still be stirred. If the promoters are not coprecipitated in this step, they can be introduced in step iiib), step iv) and/or step vii). The addition of the aqueous precipitation solution is continued until precipitation is complete. The resulting precipitate can be stirred for a further period if necessary.

Step ii)

The precipitate obtained in step i) is subsequently separated off by customary engineering methods and may, if appropriate, be washed free of undesirable water-soluble ions, e.g. nitrates.

Step iiia)

The precipitate obtained in this way can be dried at from 50 to 200° C. and subsequently milled to give a catalyst powder.

Step iiib)

As an alternative to step iiia), the precipitate obtained can be slurried and the slurry (suspension) can subsequently be spray dried in a spray dryer at from 100 to 600° C. This gives a spray-dried catalyst powder.

If spray drying (step iiib)) is chosen, promoters such as manganese, ruthenium and/or phosphorus can also be added in the form of their salts in this process step.

Step iv)

The catalyst powders produced in step iiia) or step iiib) can be calcined. The calcination is carried out in one step at final temperatures of from 300 to 1000° C., preferably from 400 to 800° C., particularly preferably from 500 to 600° C.

The calcined catalyst powders can be shaped by various methods to form shaped catalyst bodies. Thus, it is possible for the powder to be tableted, to be extruded in a screw extruder or to be extruded by means of a ram extruder to form extrudates having a particular size and shape. Shapes which can be produced are all geometric bodies which can be introduced into fixed-bed reactors. In all cases, shaping aids such as graphite or stearic acid can be mixed into the powder.

Promoters in the form of their salts can be added either before or after and/or during shaping to produce shaped catalyst bodies.

Step v)

The resulting shaped catalyst bodies are subsequently dried at from 70 to 200° C., preferably from 90 to 150° C., particularly preferably from 100 to 130° C., and then calcined. Calcination is carried out in one step at final temperatures of from 300 to 1000° C., preferably from 700 to 1000° C., particularly preferably from 800 to 950° C.

Step vi)

For the reduction, the dried and calcined shaped catalyst bodies are flushed with nitrogen at room temperature and a pressure of from 2 to 10 bar, preferably from 4 to 8 bar, is then set under a nitrogen atmosphere.

An amount of $H_2$ generally corresponding to from 30 to 70% of the nitrogen flow, preferably from 40 to 60% of the nitrogen flow, is subsequently added. The temperature is then increased from room temperature to 200–400° C., preferably to 250–350° C., particularly preferably to 280–320° C., over a period of generally from 2 to 24 hours, preferably from 5 to 15 hours. This final temperature is generally held until the desired degree of reduction has been achieved; this can be determined by means of the water of reduction given off by the shaped catalyst body. The reduced shaped catalyst body is subsequently allowed to cool to room temperature in the stream of nitrogen.

Step vii)

This step is optional. To passivate, i.e. surface-oxidize, the reduced shaped catalyst body, air is gradually added to the nitrogen stream at a rate which is sufficiently slow for the temperature in the catalyst bed not to exceed 60° C., i.e. the temperature is in the range from 20 to 60° C., preferably from 20 to 50° C., particularly preferably from 20 to 40° C. The replacement of nitrogen by air is continued until the gas stream flowing over the shaped catalyst body is 100% air.

Use of, for example, cobalt salts in the above-described process gives cobalt catalysts having a specific surface area of greater than or equal to 12 $m^2/g$, i.e. from 12 to 500 $m^2/g$, preferably from 15 to 200 $m^2/g$, particularly preferably from 18 to 100 $m^2/g$, and a porosity of $\geq 0.10$ $cm^3/g$, i.e. from 0.10 to 1.00 $cm^3/g$, preferably from 0.11 to 0.40 $cm^3/g$, particularly preferably from 0.12 to 0.20 $cm^3/g$.

It is also possible to use this method to produce mixed Ru/Co catalysts in which the proportion of Ru is from 0.01 to 10% by weight, preferably from 0.1 to 5% by weight, particularly preferably from 0.5 to 2% by weight, in each case calculated as oxide. Such a Co catalyst is produced either by coprecipitation of Co and Ru salts in step i) of the process or by addition of ruthenium salts in steps iiib), iv) and/or vi).

The catalysts produced in the abovementioned process and having an alkali metal content of $\leq 0.03\%$ by weight, in particular a sodium content of $\leq 0.03\%$ by weight, calculated as alkali metal oxide/sodium oxide, are used as all-active catalysts in the process of the present invention for preparing IPDA from IPN. However, it is also possible for catalysts which have an alkali metal content of $\leq 0.03\%$ by weight, in particular a sodium content of $\leq 0.03\%$ by weight, calculated as alkali metal oxide/sodium oxide, but have been obtained by another process which is not according to the present invention to be used in the present process for preparing IPDA from IPN.

The invention is illustrated by the following examples.

EXAMPLE 1

Production of a Largely Na-free Co Catalyst

Using a solution comprising 10% by weight of cobalt, 0.55% by weight of manganese and 0.45% by weight of $H_3PO_4$ as starting material, a largely Na-free Co catalyst was produced by means of the above process.

Table 1 reports the composition of the catalyst as was determined by elemental analysis (atomic absorption spectroscopy). The catalyst has a specific surface area of 16 $m^2/g$ and a porosity of 0.12 $cm^3/g$.

TABLE 1

|  | As Element | As Oxide |
|---|---|---|
| Co [% by weight] | 76 | 87.9 |
| Mn [% by weight] | 4.2 | 6.6 |
| P [% by weight] | 1.8 | 5.5 |
| Na [% by weight] | <0.01 | <0.01 |
| Oxidically bound oxygen | Balance to 100% by weight | |

Comparative Example 1

As comparative catalyst, an Na-containing catalyst corresponding to catalyst A of EP-A 0 742 045 was produced.

EXAMPLE 2

Preparation of IPDA

The aminative hydrogenation of IPN to IPDA is carried out at a pressure of 250 bar in a continuous process in three reactors connected in series. The largely Na-free (according to the present invention) or Na-containing cobalt catalyst is heated under a hydrogen atmosphere to 280° C. at a heating rate of 2° C./min. After 12 hours at this temperature, the temperature is brought back to the respective reaction temperature.

Isophoronenitrile (130 ml/h), ammonia (600 g/h) and 300 l/h of hydrogen are passed at about 80–100° C. in the upflow mode through the first reactor (imination reactor, 200 ml) charged with $\gamma$-$Al_2O_3$ as catalyst. The imination occurs here. The reaction mixture is fed into the first reactor (trickle-bed reactor) containing the cobalt catalyst. The temperature there is 90° C. In the third (last) reactor, the after-hydrogenation is carried out at 130° C. in the upflow mode in the presence of the cobalt catalyst. The product mixture is depressurized and cooled and analyzed by gas chromatography.

The two catalysts are compared below:

|  | Na-containing Co catalyst (Comparative Example 1) | Na-free Co catalyst (according to the present invention) |
|---|---|---|
| Total yield | 92.9 | 92.5 |
| cis/trans ratio | 68.7 | 75.8 |
| HCN elimination products (IIa and IIb) | 4.6 | 1.5 |
| Methylated by-products (IIIa and IIIb) | 0.7 | 0.1 |
| Cyclic by-product (V) | 0.4 | 2.6 |
| Amino nitrile (IV) | 0.2 | 0.1 |

A comparison of the results shows that use of a largely Na-free catalyst according to the present invention gives IPDA in about the same total yield as when an Na-containing catalyst is used. However, a higher cis/trans ratio is achieved when using the catalyst according to the present invention. In addition, the amounts of by-products which are difficult to separate off (IIa, IIb, IIIa, IIIb and IV) are lower, while the amount of by-product (V) which is easy to separate off is slightly increased.

We claim:

1. A process for preparing 3-aminome-thyl-3,5,5-trimethylcyclohexylamine (isophoronediamine, IPDA) having a cis/trans isomer ratio of at least 70/30 from 3cy-ano-3,5,5- trimethylcyclohexanone (isophotonenitrile, IPN), NH$_3$ and H$_2$ in presence of a hydrogenation catalyst comprising
   from 55 to 98% by weight of cobalt,
   from 0.2 to 15% by weight of phosphorus and
   from 0.2 to 15% by weight of manganese,
in each case calculated as oxide referring to the total weight of the catalyst,
at a temperature of from 50 to 200° C. and a pressure of from 50 to 300 bar, wherein the hydrogenation catalyst has an alkali metal content of ≦0.03% by weight, calculated as alkali metal oxide referring to the total weight of the catalyst.

2. A process as claimed in claim 1, which is carried out as a two-stage procedure comprising the following steps:
   A) reaction of IPN, NH$_3$ and H$_2$ at from 20 to 150° C. and a pressure of from 50 to 300 bar optionally in the presence of a imination catalyst;
   B) reaction of the reaction mixture obtained in step A) at from 60 to 100° C. and a pressure of from 50 to 300 bar in the presence of a hydrogenation catalyst;
where step A) and step B) are carried out either in the same reaction space or in two physically separate reaction spaces.

3. A process as claimed in claim 1, which is carried out in three physically separate reaction spaces and comprises the following reaction steps:
   a) reaction of IPN with excess ammonia at from 20 to 150° C. and pressures of from 50 to 300 bar in a first reaction space to form 3-cyano-3,5,5-trimethylcyclohexanonimine (I), optionally over an acidic metal oxide catalyst,
   b) hydrogenation of the reaction products obtained in step a) by means of hydrogen at from 60 to 100° C. and pressures of from 50 to 300 bar in the presence of excess ammonia over a hydrogenation catalyst in a second reaction space, and
   c) hydrogenation of the reaction product obtained in step b) in the presence of hydrogen and ammonia over a hydrogenation catalyst at from 110 to 160° C. and pressures of from 50 to 300 bar in a third reaction space.

4. A process as claimed in claim 3, wherein step a) is carried out at from 30 to 130° C. and/or pressures of from 100 to 250 bar.

5. A process as claimed in claim 3, wherein step b) and/or step c) are/is carried out at pressures of from 100 to 250 bar.

6. A process as claimed in claim 1, wherein the alkali metal content of a hydrogenation catalyst is ≦0.015% by weight, calculated as alkali metal oxide referring to the total weight of the catalyst.

7. A process as claimed in claim 1, wherein the alkali metal content is ≦0.01% by weight.

8. A hydrogenation catalyst comprising
   from 55 to 98% by weight of cobalt,
   from 0.2 to 15% by weight of phosphorus and
   from 0.2 to 15% by weight of manganese,
in each case calculated as oxide referring to the total weight of the catalyst.

9. A process for producing a hydrogenation catalyst as claimed in claim 8, comprising
   i) precipitating at least one of the abovementioned transition metals in the form of its carbonate, hydroxide and/or oxide from an aqueous solution comprising at least one water-soluble salt of the abovementioned transition metals by means of an aqueous solution comprising at least, one substance selected from the group consisting of ammonium carbonate, ammonium hydrogen carbonate, ammonium carbamate, ammonium oxalate, ammonium malonate, ammonia and urotropin while stirring, with or without addition of promoters in the form of their water-soluble compounds;
   ii) separating off the precipitate obtained in step i);
   iiia) drying the resulting precipitate at from 50 to 200° C. and milling it to a catalyst powder, or
   iiib) slurrying the resulting precipitate and spray drying the resulting suspension at from 100 to 600° C., with or without addition of promoters in the form of their salts, to give a spray-dried catalyst powder;
   iv) calcining the catalyst powder produced in step iiia) or iiib) at from 300 to 1000° C. and shaping it to form shaped catalyst bodies, with promoters being able, if desired, to be added in the form of their salts before or during or after shaping to form shaped catalyst bodies;
   v) drying and calcining the shaped catalyst bodies produced in step iv);
   vi) reducing the died and calcined shaped catalyst bodies in an H$_2$/N$_2$ atmosphere at elevated temperature, with the composition of the H$_2$/N$_2$ atmosphere and the temperature being varied;
   vii) optionally passivating the reduced shaped catalyst bodies at from 20 to 60° C., with promoters subsequently being applied in the form of their salts to the shaped catalyst bodies if desired.

10. A process as claimed in claim 9, wherein the precipitation in step i) is carried out using an aqueous solution comprising ammonium carbonate.

11. A process as claimed in claim 9, wherein one or more water-soluble Co salts are used in step i).

12. A process as claimed in claim 9, wherein one or mire water-soluble Mn salts and one or more water-soluble phosphorous compounds are used as promoters in step i).

* * * * *